(12) United States Patent
Greenberg et al.

(10) Patent No.: US 6,990,227 B2
(45) Date of Patent: Jan. 24, 2006

(54) METHOD FOR PRINTED CIRCUIT BOARD INSPECTION

(75) Inventors: Anat Greenberg, Hod Hasharon (IL);
 Gregory Gutarts, Kiryat Gat (IL);
 Anna Yaari, Billerica, MA (US);
 Michael Barel, Rehòvòt (IL); Jacob Nadivi, Ashdod (IL)

(73) Assignee: Orbotech LTD, Yavne (IL)

( * ) Notice: Subject to any disclaimer, the term of this patent is extended or adjusted under 35 U.S.C. 154(b) by 332 days.

(21) Appl. No.: 09/730,381

(22) Filed: Dec. 5, 2000

(65) Prior Publication Data
 US 2001/0002935 A1   Jun. 7, 2001

(30) Foreign Application Priority Data
 Dec. 5, 1999   (IL) ........................................ 133312

(51) Int. Cl.
 *G06K 9/00*   (2006.01)
(52) U.S. Cl. ...................... 382/147; 382/146; 382/148; 382/149
(58) Field of Classification Search ................ 382/141, 382/143–152; 356/237.1, 237.2, 237.3, 237.4, 356/237.5, 237.6, 237.7, 394; 250/559.01, 250/559.41; 348/87, 88, 125, 126, 92; 430/311
See application file for complete search history.

(56) References Cited

U.S. PATENT DOCUMENTS

| | | | | |
|---|---|---|---|---|
| 4,778,745 A | * | 10/1988 | Leung ........................ | 430/311 |
| 5,495,535 A | | 2/1996 | Smilansky et al. ......... | 382/145 |
| 6,111,602 A | * | 8/2000 | Kim ............................ | 348/92 |
| 6,437,862 B1 | * | 8/2002 | Miyazaki et al. ......... | 356/237.2 |
| 6,483,937 B1 | * | 11/2002 | Samuels ..................... | 382/144 |

* cited by examiner

*Primary Examiner*—Vikkram Bali
(74) *Attorney, Agent, or Firm*—Ladas & Parry LLP

(57) ABSTRACT

This invention discloses a method for printed circuit board (PCB) inspection, including providing a multiplicity of PCBs placed on an inspection panel, defining each non-identical PCB in terms of geometry and features which are to be inspected, grouping the PCBs into at least one cluster, the at least one cluster being defined in terms of an amount, location and orientation of the PCBs in the at least one cluster, creating a reference image for the panel defined by a location and orientation of the at least one cluster on the panel and inspecting the panel by comparing sensed information with the reference image.

10 Claims, 4 Drawing Sheets

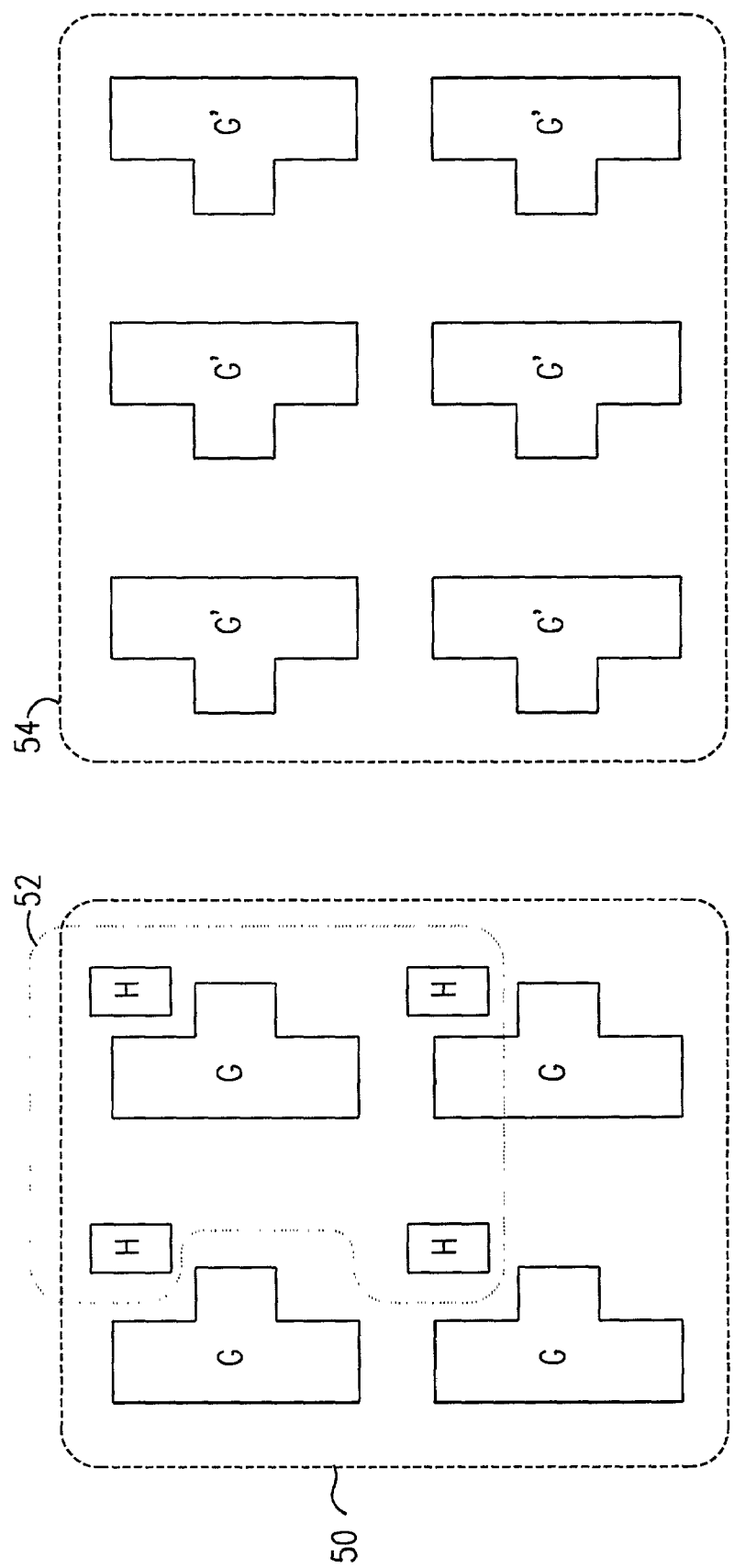

METHOD FOR PRINTED CIRCUIT BOARD INSPECTION

FIELD OF THE INVENTION

The present invention relates generally to methods for printed circuit board inspection and particularly to an improved inspection system for PCBs that can quickly and efficiently inspect any arrangement, orderly or not, of PCBs, identical or not.

BACKGROUND OF THE INVENTION

Printed circuit boards (PCBs) are generally arranged on flat panels for inspection by automated inspection systems. Reference information regarding spatial coordinates and geometry of features found on the PCB, such as pads, holes and the like, is typically input to the inspection system from a data base of computerized design software used to lay out the PCB. The inspection system senses the coordinates and geometry of the features, such as by optical sensors, and compares the sensed information to that of the data base. In this manner, the system detects which PCBs are acceptable and which have flaws.

In general, a multiplicity of the PCBs to be inspected rest on flat panels with typical dimensions of 18×24 inches. In prior art systems, reference information is generated for an entire panel. Alternatively, reference information may be generated for a single PCB. However, the PCBs must be arranged in orderly columns and rows so that the inspection system can find a reference point for each PCB from which coordinate measurements are made. For example, the lower left corner may be designated (0,0) and all measurements in (x,y) coordinates are based on that origin. Once the reference points for the PCBs have been found, the inspection system can simply inspect all of the PCBs, since they are all identical to each other without generating a reference for the entire panel.

However, prior art inspection systems cannot readily inspect the PCBs if they are not arranged in an orderly fashion or are not identical to each other.

SUMMARY OF THE INVENTION

The present invention seeks to provide an improved inspection system for PCBs that can quickly and efficiently inspect any arrangement, orderly or not, of PCBs, identical or not.

In the present invention, PCBs on a panel to be inspected are grouped into clusters. Each cluster is defined in terms of the number of PCBs in that cluster, the location of the PCBs and their orientation, the concept of orientation including mirroring. An image is created and defined by the location and orientation of each of the clusters on the panel. An image map is generated for the panel to be inspected, for use by a computerized automated inspection system. The image map includes the location and orientation of each of the clusters on the panel and the information about the geometry and features of the PCBs in each cluster. Using the image map, the inspection system commences with a first defined PCB and proceeds until all of the PCBs on the panel have been inspected.

There is thus provided in accordance with a preferred embodiment of the present invention a method for printed circuit board (PCB) inspection, including providing a multiplicity of PCBs placed on an inspection panel, defining each non-identical PCB in terms of geometry and features which are to be inspected, grouping the PCBs into at least one cluster, the at least one cluster being defined in terms of an amount, location and orientation of the PCBs in the at least one cluster, creating a reference image for the panel defined by a location and orientation of the at least one cluster on the panel, and inspecting the panel by comparing sensed information with the reference image.

In accordance with a preferred embodiment of the present invention pattern recognition methods are used to group the PCBs into the at least one cluster. Alternatively, PCBs are grouped, and their orientations defined, manually.

Further in accordance with a preferred embodiment of the present invention an image map is generated for the panel, the image map specifying the location and orientation of the at least one cluster on the panel, inputting information about the geometry and features of the PCBs into the image map, and using the image map by a computerized automated inspection system to inspect the PCBs.

Still further in accordance with a preferred embodiment of the present invention the inspection system learns attributes of, and creates and stores a reference for, each non-identical PCB.

In accordance with a preferred embodiment of the present invention the inspection system uses the image map to duplicate the stored references for duplicate locations of each individual PCB.

Further in accordance with a preferred embodiment of the present invention the reference image is used to create a mirror image of a PCB.

Still further in accordance with a preferred embodiment of the present invention the PCBs are grouped into a cluster that includes at least two sub-clusters which are not contiguous with each other.

BRIEF DESCRIPTION OF THE DRAWINGS

The present invention will be understood and appreciated more fully from the following detailed description, taken in conjunction with the drawings in which:

FIGS. 2, 3 and 4 are simplified illustrations of layouts of PCBs that can be inspected with the methods of the invention.

DETAILED DESCRIPTION OF A PREFERRED EMBODIMENT

Figure 1:
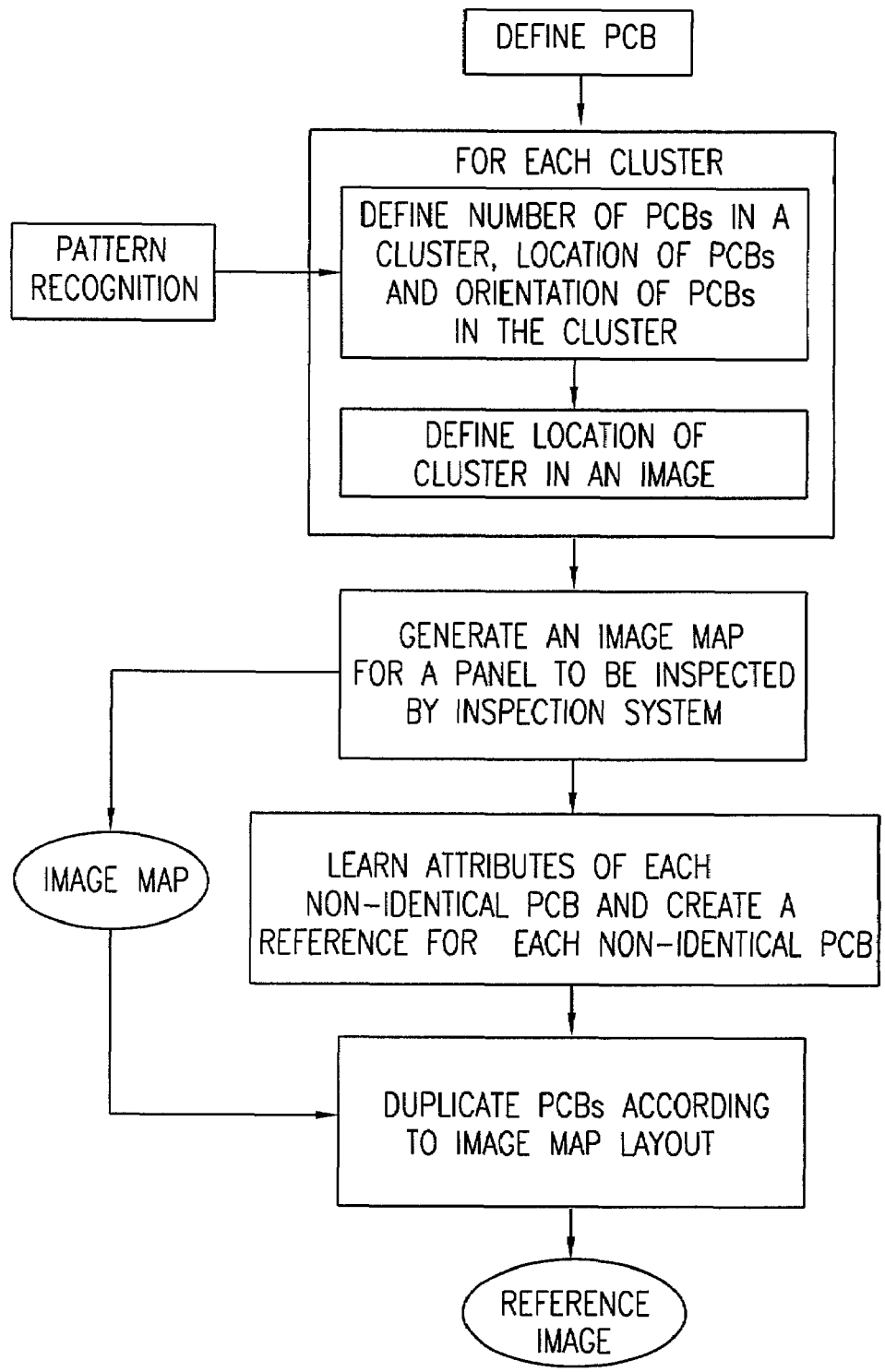
FIG. 1 is a simplified flow chart of a method for PCB inspection in accordance with a preferred embodiment of the present invention.
Figure 2:
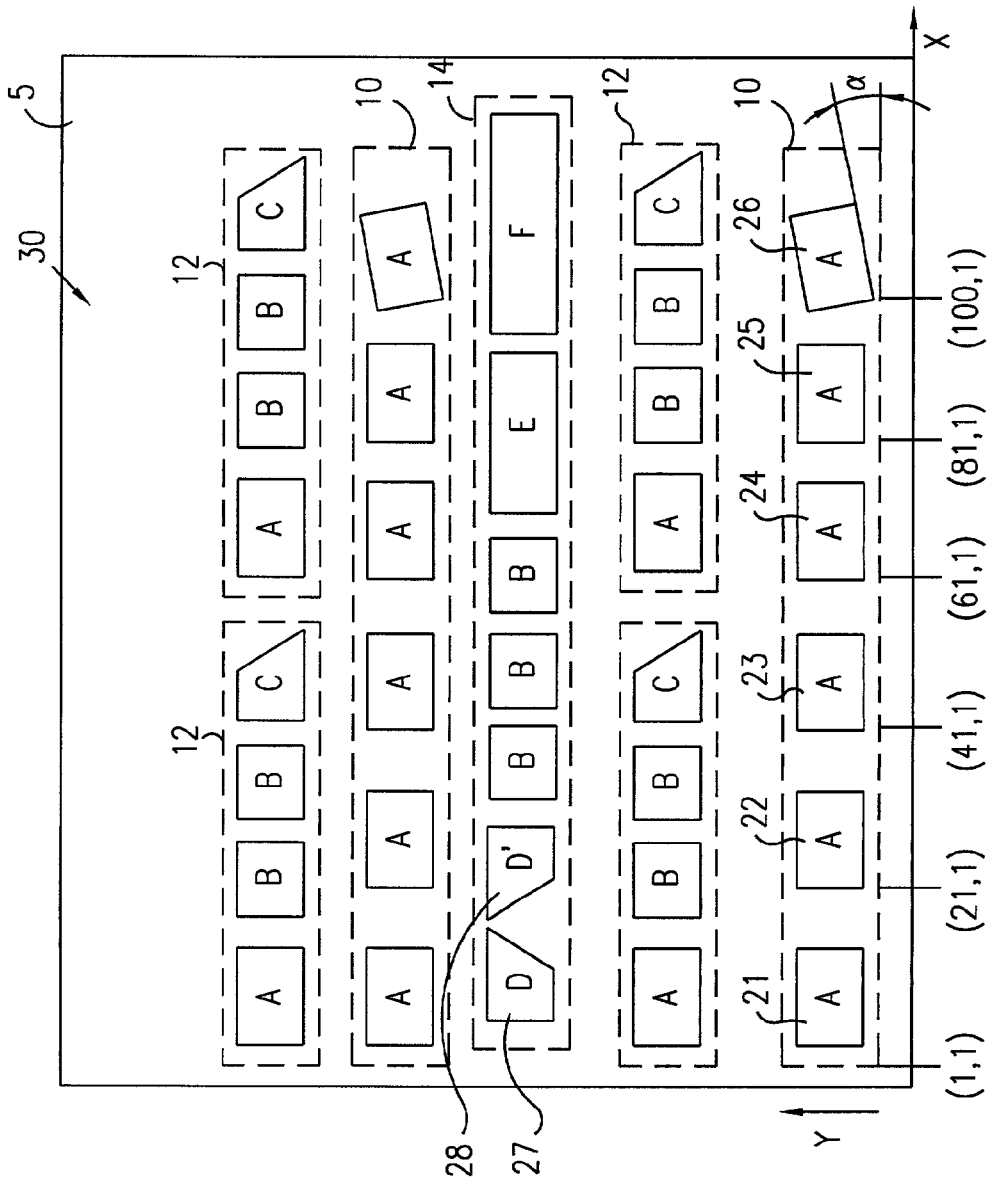

Reference is now made to FIG. 1 which illustrates a flow chart of a method for PCB inspection, in accordance with a preferred embodiment of the present invention, and to FIG. 2 which illustrates a layout of PCBs to be inspected with the method of the invention. The PCBs may rest upon a flat inspection panel 5, as in conventional inspection systems. The PCBs may include any number of non-identical PCBs, arranged in any manner.

In the method of the invention, a multiplicity of PCBs, such as PCBs A, B, C, D, E and F, are each defined in terms of geometry (shape and size) and features which must be inspected, such as holes, pads and the like. The PCBs are then grouped into one or more clusters, such as clusters 10, 12 and 14. Each cluster is defined in terms of the number of PCBs in that cluster, the location of the PCBs and their orientation. For example, cluster 10 contains 6 PCBs of type A, reference numerals 21, 22, 23, 24, 25 and 26. The dimensions of each PCB type A are, for example, 19 by 15, with reference to coordinate axes (x,y). The reference points of the PCBs are (1,1), (21,1), (41,1), (61,1), (81,1) and (100,1). The orientation of PCBs 21, 22, 23, 24 and 25 are such that the PCBs are generally aligned with coordinate axes (x,y). The orientation of PCB 26 is such that it is rotated at an angle α with respect to the x-axis. Additionally the orientation of PCBs may be mirror imaged in the same cluster, for example PCBs 27 and 28 in cluster 14. Typically a cluster includes a single type of PCB, although multiple types of PCBs may also be provided in the same cluster.

Pattern recognition methods and algorithms may be used to group the PCBs into the clusters and to determine their orientation. Such methods can be used to optimize and speed up the process of grouping the PCBs into clusters. Of course, the grouping and orientation determination can be done manually instead.

The arrangement of clusters 10, 12 and 14 on panel 5 defines an image 30. In other words, image 30 is defined by the location and orientation of each of the clusters on panel 5. FIG. 2 is just one example of a cluster arrangement, and other examples are now described with reference to FIGS. 3 and 4.

Figure 3:
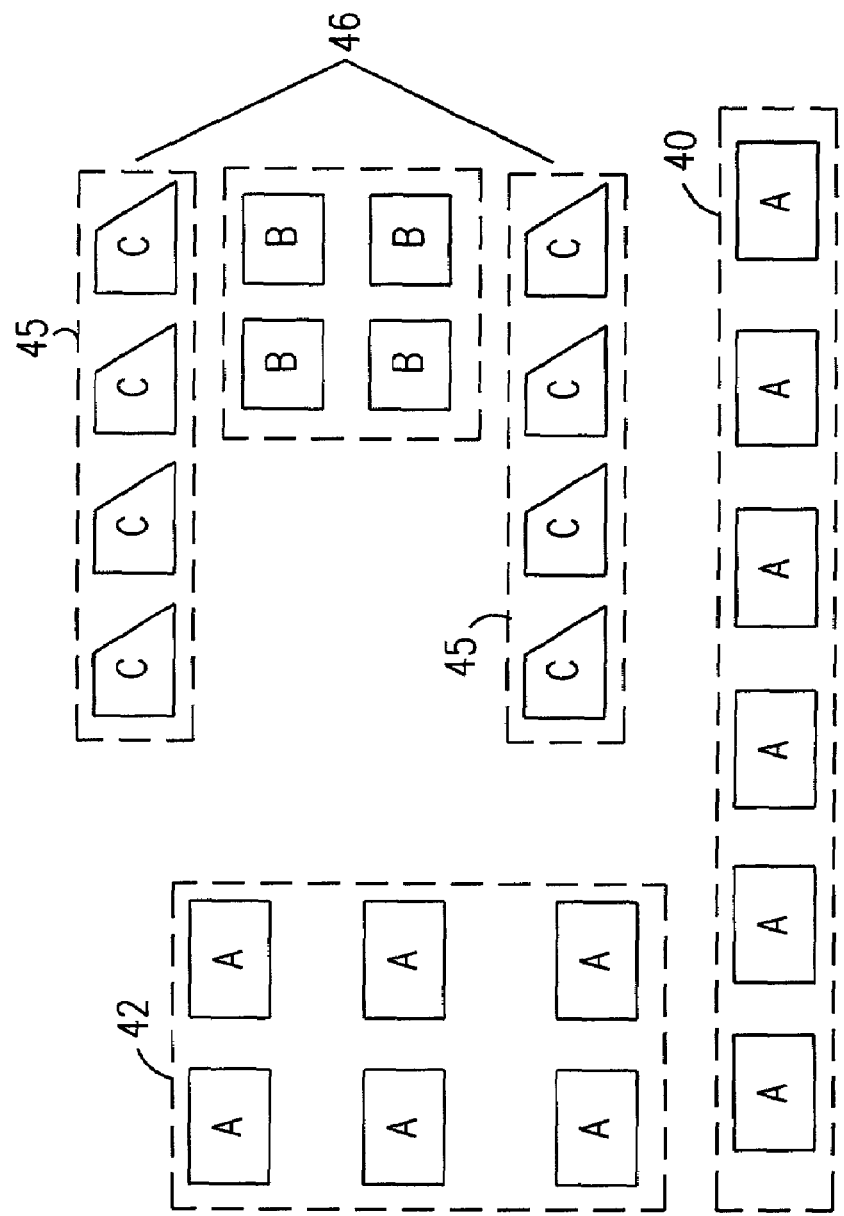

In FIG. 3, a cluster 40 of 6 identical and identically oriented PCBs A is located at the bottom of the panel, and a cluster 42 of 6 other identical and identically oriented PCBs A is on the left side of the panel, the PCBs of cluster 40 being oriented differently than those of cluster 42. A cluster 44 of 4 identically oriented PCBs B is on the middle right side of the panel. Two identical clusters 45 of 4 identical and identically oriented PCBs C are on the right side of the panel. Clusters 45 can be combined into one cluster 46 of 8 PCBs C, even though cluster 44 intervenes between clusters 45. By using cluster 46 instead of clusters 45, processing time is saved. Thus, FIG. 3 illustrates that the clusters can "overlap" one another and that clusters need not be contiguous.

In FIG. 4, a cluster 50 of 4 identically oriented PCBs G is on the left side of the panel. Partially overlapped with cluster 50 is a cluster 52 of 4 identically oriented PCBs H. Another cluster 54 of 6 identically oriented PCBs G' is on the right side of the panel. It is noted that each PCB G' of cluster 54 is the mirror image of the PCB G in cluster 50. Thus the system can conveniently define PCBs G' by simply defining them as the mirror image of G without having to waste processing time to define them all over again.

It is appreciated that any arbitrary arrangement of clusters and PCBs may be handled by the methods of the present invention.

A reference image map is generated for the panel to be inspected, for use by a computerized automated inspection system. The image map includes the location and orientation of each of the clusters on the panel and the information about the geometry and features of the PCBs therein. In accordance with a preferred embodiment of the present invention, the inspection system learns the attributes of, and creates and stores a reference for, each non-identical PCB. Using the image map, the inspection system duplicates the stored references for duplicate locations of each individual PCB and inputs the image of each non-identical PCB into its appropriate location in the image map. This step may be performed prior to inspection or "on the fly" during inspection. This increases the efficiency and operative speed required to prepare a reference image and that of the inspection system in general, and also reduces memory and disk space required.

In summary, by grouping the PCBs of the panel into clusters, the inspection system can readily inspect any regular or irregular arrangement of PCBs, by sequentially scanning the panel area.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. A method for inspecting a plurality of electrical circuits formed on a printed circuit board panel, said electrical circuits including at least two distinct electrical circuit configurations, the method comprising:

defining an image map for use in inspecting a plurality of electrical circuits formed on a printed circuit board panel, including:

obtaining at least two different references, each of said at least two references corresponding to one of at least two distinct electrical circuit configurations to be inspected;

obtaining orientation information for ones of the electrical circuits in said plurality of electrical circuits, at least some electrical circuits being oriented differently from other electrical circuits; and utilizing said at least two different references together with said orientation information to define said image map;

acquiring an optical inspection output of said plurality of electrical circuits formed on said printed circuit board panel; and employing said image map and said inspection output in a computerized automated inspection system to automatically inspect said plurality of electrical circuits.

2. The method claimed in claim 1, wherein said obtaining at least two different references comprises defining for each of said at least two different references at least one of: a shape of the reference, a size of the reference, and a composition of electrical circuit features to be inspected using the reference.

3. The method claimed in claim 2, wherein said electrical circuit features include at least one of holes and pads on said plurality of electrical circuits.

4. The method claimed in claim 1, wherein said defining an image map further comprises grouping a plurality of references into at least one cluster.

5. The method claimed in claim 4, further comprising defining for each of said at least one cluster at least one of a quantity of references included within the cluster, a type of each reference within the cluster, a location of each reference within the cluster, and an orientation of each reference within the cluster.

6. The method claimed in claim 4, wherein said grouping comprises employing pattern recognition to automatically group said references into said at least one cluster.

7. The method claimed in claim 6, wherein said employing pattern recognition further comprises automatically determining an orientation of said references.

8. The method claimed in claim 1, wherein said defining an image map further comprises learning attributes associated with each non-identical circuit configuration, said attributes to be utilized by said computerized automated inspection system to inspect said plurality of electrical circuits.

9. The method claimed in claim 1, wherein said defining an image map comprises learning features associated with each distinct electrical circuit configuration, said features to be utilized by said computerized automated inspection system to inspect said plurality of electrical circuits.

10. The method claimed in claim 1 wherein said plurality of electrical circuits formed on a printed circuit board panel define at least one printed circuit board (PCB).

* * * * *

UNITED STATES PATENT AND TRADEMARK OFFICE
CERTIFICATE OF CORRECTION

PATENT NO. : 6,990,227 B2
DATED : January 24, 2006
INVENTOR(S) : Anat Greenberg et al.

It is certified that error appears in the above-identified patent and that said Letters Patent is hereby corrected as shown below:

Title page,
Item [*] Notice, "332" should read -- 391 --.

Signed and Sealed this

Eighteenth Day of April, 2006

JON W. DUDAS
*Director of the United States Patent and Trademark Office*